United States Patent [19]

Takayanagi et al.

[11] 4,256,917
[45] Mar. 17, 1981

[54] ANHYDROUS L-LYSINE MONOHYDROCHLORIDE IN α-CYRSTALLINE FORM AND PREPARATION THEREOF

[75] Inventors: Yoshikazu Takayanagi, Yokohama; Katsuo Iizumi, Kawasaki; Masashi Miyazawa, Yokohama; Nobuyuki Yamaya, Kawasaki; Hajime Tamura, Sagamihara, all of Japan

[73] Assignee: Ajinomoto Company, Limited, Tokyo, Japan

[21] Appl. No.: 749,283

[22] Filed: Dec. 10, 1976

Related U.S. Application Data

[63] Continuation-in-part of Ser. No. 583,527, Jun. 4, 1975, abandoned.

[30] Foreign Application Priority Data

Jun. 4, 1974 [JP] Japan .................................. 49/63137

[51] Int. Cl.³ .......................................... C07C 101/24
[52] U.S. Cl. ...................................... 562/562; 426/392
[58] Field of Search ...................... 260/534 L, 501.11; 562/562

[56] References Cited

U.S. PATENT DOCUMENTS 3,527,776  9/1970  Uzuki et al. ..................... 260/501.11

OTHER PUBLICATIONS

Mellon et al., J.A.C.S., 73, 3879–3882 (1951).
Hayashi et al., Chem. Absts., 62, 9231(b), 1965.
Seto, Chem. Absts., 56, 1560(b), (1962).
Stecker et al., The Merck Index, Merck & Co., Inc., Rahway, N.J., 8th Ed., p. 633 (1968).

Primary Examiner—Joseph E. Evans
Assistant Examiner—G. T. Breitenstein
Attorney, Agent, or Firm—Oblon, Fisher, Spivak, McClelland & Maier

[57] ABSTRACT

A novel crystalline form of anhydrous L-lysine monohydrochloride has been found. The novel crystals do not become agglomerated or hardened when packaged. The crystals are formed when the corresponding dihydrate crystals having a sodium content equal to or less than 4 ppm* are dried in a chamber maintained at a temperature equal to or greater than 115° C.

*Na/L-Lys.HCl

4 Claims, 3 Drawing Figures

ANHYDROUS L-LYSINE MONOHYDROCHLORIDE IN α-CYRSTALLINE FORM AND PREPARATION THEREOF

CROSS REFERENCE TO RELATED APPLICATION

This application is a CIP of U.S. application Ser. No. 583,527, filed on June 4, 1975.

BACKGROUND OF THE INVENTION

1. Field of the Invention

This invention relates to novel crystals or anhydrous L-lysine monohydrochloride, termed α-crystals, and to a process for producing the same.

2. Description of the Prior Art

L-lysine is useful as a feed supplement, as a component in infusion solutions and in many other areas. It is usually commercially supplied in anhydrous form as a monohydrochloride salt.

A general process for the production of the anhydrous crystals comprises concentration of a solution of L-lysine monohydrochloride, followed by cooling to yield dihydrate crystals of L-lysine monohydrochloride. The dihydrate crystals are subsequently dried to form the anhydrate crystals. The drying of the dihydrate crystals is usually carried out at low temperatures, such as near 100° C. or lower, under atmospheric pressure or preferably under reduced pressure. When amino acid crystals are dried at higher temperatures, for example at 120° C. for 3 hours, the dried products commonly become slightly yellow or brown. Accordingly, their commercial value is lowered. Using this method, the commercial anhydrous L-lysine monohydrochloride powder occasionally hardens and conglomerates into a solid block when placed in a vinyl package, causing a large problem in its supply.

SUMMARY OF THE INVENTION

It has now been found that a novel β-form of anhydrous L-lysine monohydrochloride crystals is metastable, and that the new crystals are highly resistant to conglomeration when packaged. The new α-crystals are produced, for example, when dihydrate crystals having a sodium content equal to or less than 4 ppm are dried at temperatures equal to or higher than 115° C. under atmospheric pressure.

*Na/L-Lys.HCl, i.e., the value of the sodium content of the dihydrate crystals is given as that value necessary to result in the stated sodium content (ppm) for the dried anhydrate crystals.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

One critical feature in the formation of the novel α-crystal-line anhydrous L-lysine monohydrochloride salt is the maintenance of a sufficiently high temperature ($\geq 115°$ C.) in the heating chamber when the corresponding dihydrate crystals are dried. As mentioned above, chambers heated to rather low temperatures only have been employed in the past. One reason is that the dihydrate crystals lose all water of hydration at a relatively low temperature, e.g., 40° C. (Seto, Bunseki Kagaku 9,939–945(1960)). Thus, there has heretofore been no need to heat in higher ambient temperatures such as those used in this invention. However, it has now been found that the completely new α-anhydrate crystal is formed if the temperature in the heating chamber is maintained at 115° C. or higher.

It has also been found that the sodium ion content of the dihydrate crystals critically affects the crystalline nature of the anhydrous form. As long as the Na-content of the dihydrate crystals is less than 4 ppm*, the α-anhydrate will be formed when the dihydrate crystals are dried in accordance with the conditions of the present invention. The potassium content has only an insignificant, if any, effect on the formation of the α-crystals.

The formation of the novel α-crystals of the invention depends upon both the Na-content of the dihydrate crystals and the heating rate used during the drying operation. The rate at which the dihydrate crystals are heated when placed in an oven at a temperature of 115° C. or higher is sufficient to ensure production of the α-crystals when the Na-content of the dihydrate crystals is equal to or less than 4 ppm*.

*Na/L-Lys.HCl.

The new α-crystal is clearly different from the known β-crystal. This is shown below by the results of the following diagnostic measurements: powder X-ray diffraction pattern; infrared spectrum; decomposition point, hygroscopic properties and the like. The α-crystal used for these measurements was produced in Example 1, Run No. 2; while the β-form crystal employed as a control was produced in Example 1, Run No. 6.

1. Powder X-ray Diffraction

Figure 1:
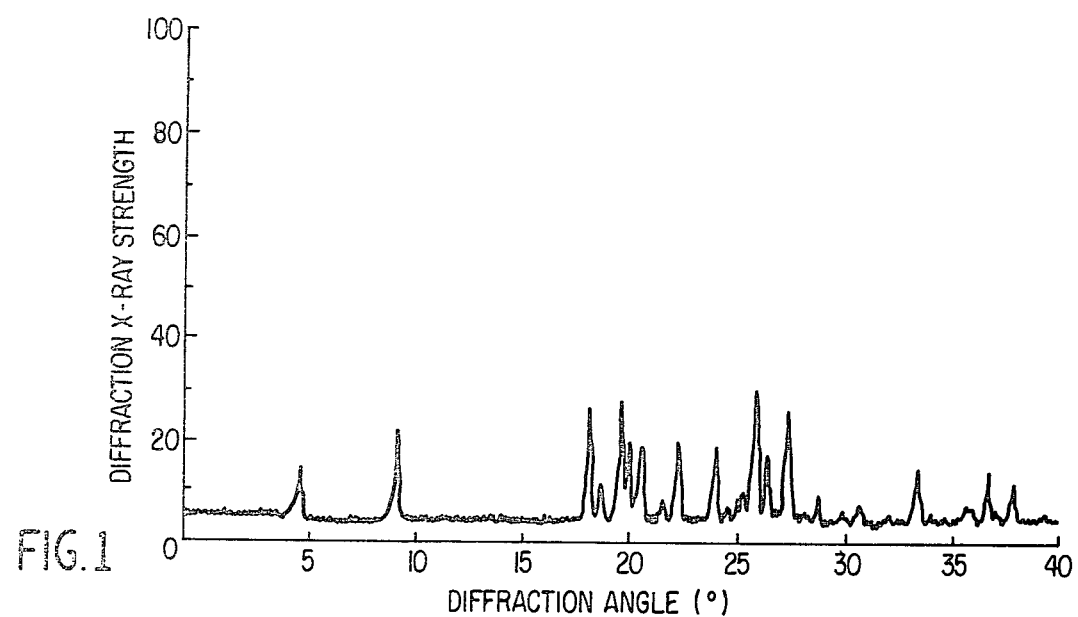
FIGS. 1 and 2 show the powder X-ray diffraction patterns of the α- and β-L-lysine monohydrochloride crystals, respectively.
Figure 2:
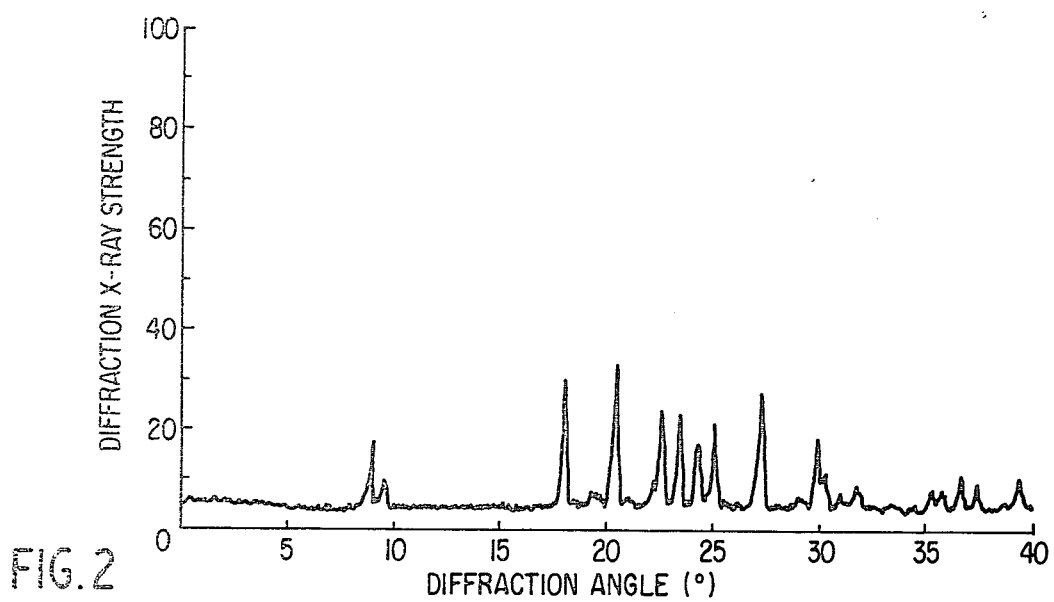

The powder X-ray diffraction pattern at angles of less than 30° C. (CuKα, 30 KV, 15 mA(Ni-filter)) of the α-crystal is shown in FIG. 1, and that of the β-crystal is shown in FIG. 2. The diffraction angles of the major peaks are shown in Table 1.

TABLE 1

| | |
|---|---|
| α-Form Crystal: | 4.5, 9.0S*, 18.1S, 18.6, 19.5S, 19.9, 20.6, 22.2, 24.0, 25.7S, 26.3, 27.3S, 33.4, 36.6, 37.8 |
| β-Form Crystal: | 9.0, 9.6, 18.0S, 20.4S, 22.6, 23.4, 24.3, 25.1, 27.2S, 29.8, 36.6, 39.3 |

*S: Strong

This diffraction data is also summarized in Table 2 which contains the intensity ratio for each crystal form as a function of interplanar spacing.

TABLE 2

| α-form | | β-form | |
|---|---|---|---|
| Interplanar spacing (A) | $I/I_1$* | Interplanar spacing (A) | $I/I_1$ |
| 19.6 | 39 | 9.82 | 45 |
| 9.82 | 69 | 9.60 | 7 |
| 4.90 | 86 | 9.21 | 19 |
| 4.77 | 27 | 4.92 | 89 |
| 4.55 | 90 | 4.57 | 10 |
| 4.46 | 62 | 4.48 | 7 |
| 4.39 | 20 | 4.35 | 100 |
| 4.31 | 60 | 4.23 | 9 |
| 4.13 | 13 | 4.00 | 28 |
| 3.70 | 56 | 3.93 | 68 |

TABLE 2-continued

| α-form | | β-form | |
|---|---|---|---|
| Interplanar spacing (A) | I/I₁* | Interplanar spacing (A) | I/I₁ |
| 3.63 | 10 | 3.80 | 63 |
| 3.56 | 16 | 3.66 | 43 |
| 3.53 | 21 | 3.54 | 59 |
| 3.46 | 100 | 3.49 | 6 |
| 3.39 | 50 | 3.41 | 6 |
| 3.26 | 84 | 3.28 | 78 |
| 3.17 | 6 | 3.18 | 3 |
| 3.11 | 17 | 3.08 | 7 |
| 3.00 | 8 | 3.06 | 7 |
| 2.92 | 14 | 2.99 | 46 |
| 2.79 | 5 | 2.97 | 21 |
| 2.68 | 40 | 2.95 | 24 |
| 2.63 | 7 | 2.94 | 9 |
| 2.53 | 12 | 2.88 | 10 |
| 2.51 | 11 | 2.83 | 7 |
| 2.45 | 36 | 2.81 | 15 |
| 2.37 | 28 | 2.70 | w |
| | | 2.67 | w |
| | | 2.60 | w |
| | | 2.55 | 14 |
| | | 2.51 | 16 |
| | | 2.45 | 26 |
| | | 2.40 | 16 |
| | | 2.28 | |

*I₁ is the intensity of the strongest diffraction peak.

Figure 3:
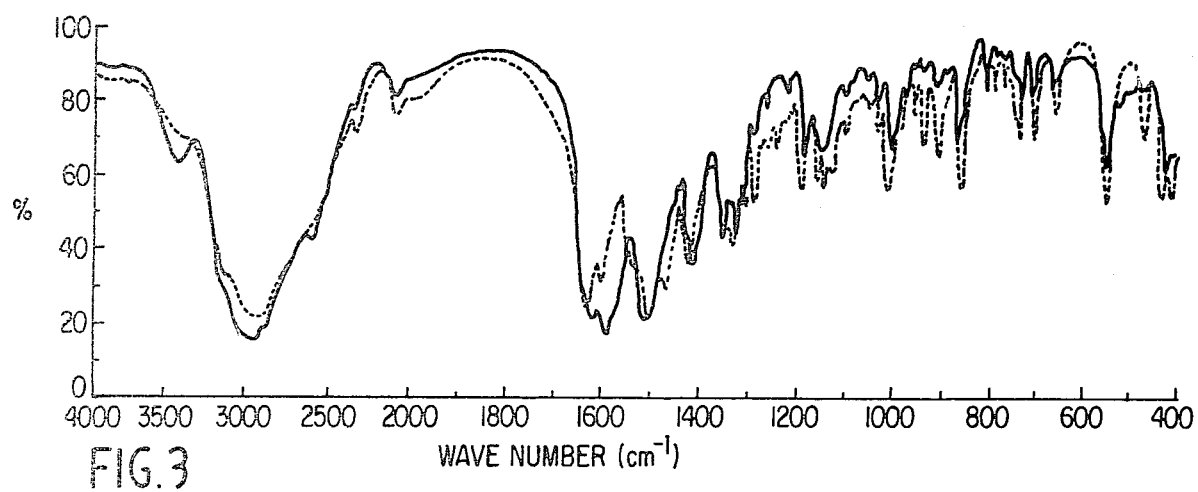
FIG. 3 shows the infrared spectra of both the α and β crystals.

2. Infrared Spectra:

The Infrared spectra of both crystals pelleted with potassium bromide are shown in FIG. 3. The full line represents the α-form crystal, and the dashed line represents the β-form crystal.

3. Elemental Analysis:

| | C | H | N | Cl |
|---|---|---|---|---|
| α-Form Crystal | 39.49% | 8.29% | 15.32% | 19.39% |
| Calculated value | 39.46 | 8.28 | 15.34 | 19.41 |

4. Optical Rotation:

α-Form crystal: $[\alpha]_D^{20} = +21.0°$ (C-8,6NHCl)

Commercial Lys HCl: $[\alpha]_D^{20} = +20.5° - +21.5°$ (C-8,6NHCl)

(β Form)

5. Melting Point:

α-Form Crystal: 246°-249° C. (decomposition)

Commercial Lys HCl: 263° C. (decomposition) (β-Form-)

6 Hygroscopic and Conglomeration Properties:

These properties are indicated by the results shown in Table 3. In the experiments described, the samples were the products of Example 1 at the drying temperatures noted.

TABLE 3

| | | Hygroscopicity Test *1 | | | Conglomeration Test *3 | |
|---|---|---|---|---|---|---|
| Drying Temperature | Crystal Form | RH32% | *2 RH52% | RH76% | At 60° C. for 15 hrs | At room temp. for 6 months *4 |
| 130° C. | α | 0.08% | 1.06% | 3.78% | Not. Cong. *5 | Not Cong. |
| 120 | α | 0.13 | 1.06 | 3.59 | Not. Cong. *5 | Not Cong. |
| 110 | α + β | 0.18 | 0.73 | 1.55 | 15 hrs. | Cong. |
| 100 | α + β | 0.11 | 0.59 | 1.04 | 8 | " |
| 90 | | 0.24 | 0.35 | 0.36 | 5 | " |

*1 1 kg of sample was kept at each humidity at 20° C. for 24 hours. The increase in weight was measured and is tabulated as follows:

$$\frac{\text{Weight after 24 hours} - \text{Initial weight}}{\text{Initial weight}} \times 100$$

*2 RH = Relative humidity
*3 A 10 kg sample was sealed in a vinyl package (polyethylene, 80 μm thick). The time for sample conglomeration and hardening into a solid block was observed.
*4 From the middle of September to the middle of March
*5 Cong = Conglomerated As can be seen from this table, the unpackaged α-form crystal is more hygroscopic than the unpackaged β-form crystal, at higher humidities. This further indicates the difference between the two forms. However, the α-form crystal is not conglomerated when stored in a vinyl package, whereas the β-form crystal and the mixture of the α-form and β-form crystals are conglomerated even when packaged. Thus, the new α-form is highly advantageous for commercial packaging.

7. Transformation to β-Form:

When α-form crystals were placed in an atmosphere of 76% relative hymidity at 40° C. for 15 hours, the crystals were entirely conglomerated and completely changed to β-form, once again indicating the existence of two separate crystal types.

Having generally described this invention, a further understanding can be obtained by reference to certain specific examples which are provided herein for purposes of illustration only and are not intended to be limiting unless otherwise specified.

EXAMPLE 1

2400 kg samples of L-lysine monohydrochloride dihydrate crystals, which were obtained from a commercial plant continuously producing lysine monohydrochloride (by the fermentation method), were dried using a horizontal type continuous fluidized bed dryer (mean residence time: 2 hours). The dried substances were all pure white. The drying temperatures and several properties of the dried products are summarized in Table 4.

TABLE 4

| Run No. | Drying Temperature | Moisture Content | Sodium Content | Potassium Content | Crystal Form |
|---|---|---|---|---|---|
| 1 | 130° C. | 0.08% | 4 ppm | 17 ppm | α |
| 2 | 120 | 0.09 | 3 | 8 | α |
| 3 | 115 | 0.09 | 3 | 3 | α |
| 4 | 110 | 0.16 | 3 | 6 | α + β |
| 5 | 100 | 0.18 | 2 | 3 | α + β |
| 6 | 90 | 0.22 | 4 | 7 | β |

Samples were withdrawn at the end of each drying process. The moisture content was determined by weight loss upon subsequent drying at 105° C. The sodium and potassium contents were determined by flame analysis. The crystal form was determined by powder X-ray diffraction.

As can be seen, when the temperature of heating was greater than 115° C. and the sodium content was sufficiently low, i.e., ≦4 ppm, α-crystals only were obtained. Under the other conditions shown, either mixtures of α and β crystals, or β crystals only, were obtained.

EXAMPLE 2

Approximately 300 mg samples of L-lysine monohydrochloride dihydrate crystals, containing different amounts of sodium chloride, were prepared and heated to 120° C. at the rate of 1.2° C./min. using a thermobalance (made by Rigaku Kenki Co.). The crystal forms of the heated samples were determined by X-ray diffraction, and are shown in Table 5.

TABLE 5

| Sodium Content* | Crystal Form |
| --- | --- |
| 7 ppm | α + β (β-form rich) |
| 50 ppm | α + β (β-form rich) |
| 200 ppm | β |
| 301 ppm | β |

*Na/L-Lys . HCl

EXAMPLE 3

About 5 g of L-lysine monohydrochloride dihydrate crystals were heated at 105° C. for 3 hours. The optical rotation value and the powder X-ray diffraction pattern of the heated sample were measured. The optical rotation was $[\alpha]_D^{20} = +21.1°$ (C=8,6N HCL). This is consistent with the value of L-lysine monohydrochloride anhydrate. The X-ray diffraction pattern of the heated sample also indicated that the sample was the anhydrate crystal consisting of a mixture of the α-form and the β-form.

EXAMPLE 4

Dihydrate crystals of L-lysine monohydrochloride, having a sodium content of 4 ppm, were heated at the rates shown in Table 6.
*Na/L-Lys.HCl.

TABLE 6

| Heating Rate (°C./min) | Crystal Form |
| --- | --- |
| 1 | α |
| 3 | " |
| 5 | " |
| 10 | " |
| 20 | " |

EXAMPLE 5

Both the sodium content of dihydrate crystals of L-lysine monohydrochloride and the heating rate were varied as shown in Table 7. The nature of the crystal form obtained is also shown in the Table.

TABLE 7

| Sodium Content* (ppm) | Heating Rate (°C./min) | Crystal Form |
| --- | --- | --- |
| 28 | 1 | α + β |
| 28 | 20 | α |
| 68 | 20 | α + β |

*Na/L-Lys . HCl

Having now fully described this invention, it will be apparent to one of ordinary skill in the art that many changes and modifications can be made thereto without departing from the spirit or scope of the invention set forth herein.

What is claimed as new and intended to be covered by letters patent is:

1. Anhydrous L-lysine monohydrochloride crystals having the X-ray diffraction pattern of FIG. 1.

2. A process for producing anhydrous α-L-lysine monohydrochloride crystals, which comprises drying L-lysine monohydrochloride dihydrate crystals, which have a sodium content equal to or less than 4 ppm, at a temperature equal to or greater than 115° C., at a rate of temperature increase of at least 1° C./min.

3. The process of claim 2, which comprises heating said dihydrate crystals in an oven maintained at a temperature equal to or higher than 115° C.

4. Anhydrous α-L-lysine monohydrochloride crystals prepared by the process of claim 2.

* * * * *